United States Patent [19]

Krsek

[11] Patent Number: 4,602,008

[45] Date of Patent: Jul. 22, 1986

[54] ALKYLATED ETIOCHOLANOLONES AND USE AS AN ANTI-DIABETIC, ANTI-OBESITY AND ERYTHROPOIETIC AGENT

[75] Inventor: George Krsek, Culver, Ind.

[73] Assignee: Progenics, Inc., New York, N.Y.

[21] Appl. No.: 681,826

[22] Filed: Dec. 14, 1984

[51] Int. Cl.⁴ ............................................. A61K 31/56
[52] U.S. Cl. .................................. 514/178; 260/397.4
[58] Field of Search ...................... 514/178; 260/397.4

[56] References Cited

U.S. PATENT DOCUMENTS 4,507,289  3/1985  Coleman et al. .................... 514/170

Primary Examiner—Elbert L. Roberts
Attorney, Agent, or Firm—Ostrolenk, Faber, Gerb & Soffen

[57] ABSTRACT

16-Alkylated and 16-alkylated-7-hydroxy 5β-androstan-3-ol-17-one, and the esters and ethers thereof, are used as an anti-diabetic, anti-obesity and erythropoietic agent in mammals.

18 Claims, No Drawings

ALKYLATED ETIOCHOLANOLONES AND USE AS AN ANTI-DIABETIC, ANTI-OBESITY AND ERYTHROPOIETIC AGENT

BACKGROUND OF THE INVENTION

The major function of the adrenal gland is to regulate metabolism in the body so that an intermittent intake of food can be regulated to maintain a constant metabolite supply to the cells. This is accomplished by producing steroid hormones which can control the conversion of incoming nutrients, such as aminoacids, glucose and fats into storage depots from which they can thereafter be released or interchanged, allowing a continuous flow of optimum energy and growth factors to the cells.

The steroid hormones are divided mainly into three classes. The first is glucocorticoids (cortisol), also known as gluconeogenic or diabetogenic steroids, which can convert aminoacids into glucose for direct use or store the glucose as glycogen for later use. Cortisol can therefore have an anti-anabolic effect through the depletion of aminoacids needed for protein synthesis and a diabetogenic effect through the direct release of glucose from the glycogen store.

A glucocorticoid excess, resulting from an excess of the pituitary hormone, adrenal cortico-trophic hormone (ACTH), which controls cortisol production, causes Cushing's Syndrome, an uncommon disease. Intake of an excess amount of cortisol from pharmacological use of steroids can also cause Cushing's Syndrome or Cushingoid-like disorders (hypercorticosteroidism, or more briefly hypercorticoidism) which are progeric in that they resemble the symptoms of the diseases of aging, e.g. obesity, hypertension, diabetes, renal stones, osteoporosis, mental disorder, menstrual disturbance, susceptibility to infection and poor wound healing.

The second category of steroids is known as the adrenal androgens. Dehydroepiandrosterone (DHEA) is the principal representative of this category. The adrenal androgens which have an anabolic action are produced with puberty, reach a peak in early adulthood and then, beyond the age of 50, decline to very low levels. Secretion of ACTH, which also controls corticosteroid production, shows no such age related fluctuation.

The third category of adrenal steroids is the mineralocorticoids (aldosterone) which control the mineral balance of the body and is partially under ACTH control in that ACTH accelerates the conversion of cholesterol to all adrenal steroids.

When the body is subjected to stress, physical or mental, e.g. injury, cold, starvation or threats, real or imagined, ACTH stimulates the adrenal cortex to produce steroids in increased amounts in order to provide the body with resources necessary for response to the stress, storage or release of glucose when needed, lipid deposition or mobilization in order to maintain the energy equilibrium of the body under conditions where extra energy may be needed and/or starvation of the cells becomes a possibility.

Under normal conditions, ACTH stimulates the adrenals to secrete both cortisol and DHEA. In the aging individual, cortisol is stimulated but DHEA is not, thus resulting in relative hypercortisolism.

It has been shown that DHEA is useful in the treatment of diabetes in mutant mice and treatment of adult-onset diabetes in obese individuals. DHEA is also known to be useful in the treatment of obesity. The genetic form of diabetes in mice is associated with hypercorticosteroidism. Hypercorticosteroid syndromes can occur as a result of excessive ACTH production due either to stress, hypofunction of the adrenal glands, pituitary tumors, ectopic ACTH production or administration of pharmacologic doses of cortisol.

DHEA is metabolized in the body. A major metabolite is etiocholanolone (5-$\beta$-androstan-3-$\alpha$-ol-17-one, (hereinafter referred to as $\alpha$-ET) and in normal individuals it is excreted in amounts of about 0.5 mg/100 ml. $\beta$-etiocholanolone (5-$\beta$-androstan-3-$\beta$-ol-17-one, hereinafter referred to as $\beta$-ET), is a minor metabolite in man. Even when large quantities are administered, there is a significant conversion of the 3$\beta$ to the 3$\alpha$-hydroxy compound. Kappas, et al, *The Thermogenic Effect and Metabolite Fate of Etiocholanolone in Man*, J. Clin. Endocrin. & Metab., 18, 1043–1055 (1958). In a diabetic individual, the quantity of $\alpha$-ET excreted is significantly less than in the normal individual.

$\alpha$-ET had been considered to be an inert end product whose sole fate was conjugation and excretion until it was shown that in its free (unconjugated) state, it had highly potent pyrogenic effects when injected intramuscularly in males, less potency in females and none in other species. No febrile reaction results when $\alpha$-ET is administered intravenously, or orally, or when $\beta$-ET is administered by any route. Kappas, et al., *Thermogenic Properties of Steroids, in Methods in Hormone Research*, Dorfman Ed. Vol. 4, p. 1 (New York & London Academic Press) (1965).

It is known that erythropoietic activity is exhibited by metabolites of certain androgenic, anabolic, or progestational steroids. Thus, Levere et al. Proceedings of a Symposium held in conjunction with the American Society of Hematology, Dec. 4, 1971, Chapter III, discloses that $\alpha$-etiocholanolone possesses erythropoietic activity. Jepson, ibid., Chapter II, disclosed that nandrolene (19-nortestosterone; 17-$\beta$-hydroxy-19-nor-4-androstan-3-one), an anabolic steroid, possesses erythropoietic activity similar to testosterone. This substance, however, has the drawback of exhibiting androgenic side-effects. It is known in the form of its decanoate, described in DeWitt et al U.S. Pat. No. 2,998,423.

Copending U.S. patent application Ser. No. 515,354 filed July 19, 1983, Ser. No. 566,222 filed Dec. 28, 1983, and Ser. No. 556,223 filed Dec. 28, 1983, respectively, describe the administration of certain DHEA compounds, $\alpha$- and $\beta$-ET in reproducing the effects of DHEA in antagonizing the effects the hypercortisolism.

It has now been determined that 16-alkylated and 16-alkylated-7-hydroxy etiocholanones are useful as an erythropoietic, anti-diabetic or anti-obesity agent in mammals. It is, therefore, the object of this invention to provide a new group of steroid compounds and for their use as an erythropoietic, anti-diabetic or anti-obesity agent. This and other objects of the invention will become apparent to those skilled in this art from the following detailed description.

SUMMARY OF THE INVENTION

This invention relates to new steroid compounds and their use as an anti-diabetic, anti-obesity or erythropoietic agent and more particularly, to 16-alkylated and 16-alkylated-7-hydroxy 5$\beta$-androstan-3-ol-17-one, and the esters and ethers thereof. The compounds are used to induce an anti-diabetic, anti-obesity or erythropoietic effect in a mammal.

DESCRIPTION OF THE INVENTION

The new compounds of the present invention are 16-alkylated and 16-alkylated-7-hydroxy 5β-androstan-3-ol-17-one, and the esters and ethers thereof. The C-3 hydroxy group can be in either the α or β position. It is presently preferred that the 3-hydroxy group be in the β position. The C-16 group can be a lower alkyl or lower alkylene group, that is, a group containing one to about four carbon atoms. Methyl and methylene groups are presently preferred.

The 16-alkylene group can be introduced into the molecule by treating the 5β-androstan-3-ol-17-one, or 5β-androstan-3,7-diol-17-one, with an aldehyde in the presence of a suitable base followed by treatment of the product with acid and base, as shown in Examples 2 and 3 below. The 16-alkylene group can then be reduced to a 16-alkyl group with hydrogen in the presence of a platinum or paladium catalyst in the known manner. The 5β-andro-stan-3-ol-17-one compounds are known. The 5β-androstan-3,7-diol-17-one can be prepared from chenodeoxycholic acid (or the corresponding 3β compound) as described in Example 1 below.

The 3 and/or 7 esters of the aforementioned compounds can be prepared in the conventional fashion using pharmaceutically acceptable acids, which may be either inorganic or organic. Examples of inorganic acids include hydrochloric, sulphuric and phosphoric, while the saturated or unsaturated organic carboxylic acids having 1–18 carbon atoms can be employed. Acetic, formic, propionic, butyric, valeric, capric, decanoic, diethyl acetic, cyclopentylpropionic, benzoic, phenylacetic, phenylproprionic, malonic, succinic, glutaric and tartaric acids are typical of the organic carboxylic acids which can be used. The 3 and/or 7 ethers can be prepared in the conventional fashion from an aliphatic, aromatic or araliphatic or heterocyclic hydrocarbon. Suitable ether groups include methoxy, ethoxy, propoxy, benzyloxy and phenylethoxy. It will be understood that the esters can be made as the sodium, potassium or ammonium salts or made into the combined esters of an alcohol such as cetyl, dodecanoate and the like to provide a compound having a more lipid soluble moiety in order to provide better absorption across the mucosal barrier after which the body would convert the product to the sodium salt of the compound.

In accordance with the present invention, the steroid compounds are administered to an individual in order to provide an anti-diabetic, anti-obesity or erythropoietic effect. The compounds can be administered orally and the usual array of oral dosage forms can be used. For example, tablets can be prepared by combining the compounds of the present invention with conventionally used binders and excipients. If desired, the compounds can be administered in a finely dispersed form, for example, as a finely dispersed powder or solution which is typically mixed with the food diet. In general, the administration amount to an average 70 kilo individual will be about 100–4,000 mg per day and preferably about 500–1,000 mg. Unit dosage administration forms will generally contain about 100–1,000 mg, preferably about 200–400 mg of the compounds. When combined with a diet, the compounds are usually used in an amount of up to about 1% by weight thereof. The compounds can be dissolved in a suitable solvent such as acetone, which is then mixed with food, and thereafter the solvent is evaporated to leave the compounds in finely dispersed powder form thoroughly mixed throughout the food.

Alternatively, the compounds can be administered parenterally, using the conventional array of parenteral dosage forms, thereby allowing for less frequent administration and lower dosages. In general, unit dosages will contain about 10–200 mg, preferably about 20–40 mg, of the compounds. The usual administration amount for an average 70 kilo individual will be about 700–2,000 mg, preferably about 900–1,100 mg, per day in single or divided administrations.

In order to further illustrate the present invention, various examples are set forth below. In these examples, as well as throughout this specification and claims, all parts and percentages are by weight at all temperatures in °C. unless otherwise specified.

EXAMPLE 1

200 grams of chenodeoxycholic acid were dissolved in 2.4 liters of methanol and 140 grams of hydrogen chloride were added. The mixture was heated at reflux for 2 hours, cooled to room temperature, 5 liters of toluene added and the mixture was washed free of acid with potassium carbonate. The toluene/methanol was removed in vacuo and the residue dissolved in 3 liters of dry toluene.

310 grams of magnesium turnings in 500 ml of tetrohydrofuran were treated with 2 kg of bromobenzene in 4 liters of tetrahydrofuran at reflux. After all of the bromobenzene had been added, the mixture was refluxed for 1 hour.

The toluene solution was added at reflux to the magnesium bromobenzene over a period of several hours and the resulting mixture refluxed for 16 hours. The mixture was cooled to room temperature and added to a mixture of 1500 ml hydrochloric acid/16 kg ice. The layers were separated, the toluene layer taken to dryness in vacuo and the residue dissolved in 3 liters of a mixture of acetic acid/acetic anhydride and refluxed for 2 hours. The reaction mixture was then concentrated in vacuo to dryness and the residue dissolved in 4 liters of benzene and washed free of acid with potassium carbonate. The benzene solution was dried and reacted with 60 grams of N-bromosuccinimide in 1 liter of benzene under the influence of a high intensity light for 20 minutes. The mixture was then refluxed until the evolution of hydrogen bromide vapor ceased. The mixture was treated again with 60 grams of the N-bromosuccinimide in 1 liter of benzene and light for 15 minutes, cooled to room temperature and washed with water.

The benzene solution was taken to dryness in vacuo and the residue dissolved in 4 liters of acetone and treated with 100 grams of sodium acetate at reflux to yield the 3α,7α,21-triacetate of 24,24-diphenyl-Δ-20,22-choladiene. The acetone was removed in vacuo and the residue was washed with water and dried. The dry residue was then dissolved in 3 liters of acetic acid and 400 ml of benzene which was treated with a solution of 200 grams of chromic acid in 400 ml of water over 2 hours. The excess chromic acid was quenched with sodium bisulfite and the mixture concentrated in vacuo to 500 ml where upon 4 liters of toluene were added. The toluene was washed free of acid and taken to dryness in vacuo.

The residue was dissolved in 2 liters of acetic anhydride and 10 grams of p-toluene sulfonic acid were added. The mixture was then distilled over 6 hours to remove most of the acetic anhydride, 3 liters of benzene were added and the benzene layer washed free of acid with sodium bicarbonate. The benzene solution was concentrated to 700 ml and 3 liters of acetic acid were added. A solution of 100 grams of chromic acid in 200 ml of water was added over 2 hours, the excess chromic acid quenched with sodium bisulfate, the mixture concentrated to near dryness and then 2 liters of toluene were added. The toluene was washed free of acid and taken to dryness in vacuo. The residue was saponified with 200 grams of sodium methoxide in 2 liters of methanol. 80 grams of 5$\beta$-androstan-3$\alpha$,7$\alpha$-diol-17-one having a melting point of 181°-184° C. were isolated. The optical rotation was +42°.

EXAMPLE 2

A mixture 20 grams of 5$\beta$-androstan-3$\alpha$,7$\alpha$-diol-17-one, 10 grams of paraformaldehyde, 33 grams of dry dimethylene hydrochloride and 175 ml of isoamyl alcohol was refluxed for 3 hours and then cooled at 5° C. overnight. 300 ml of 1:9 HCl/H$_2$O was added and the mixture diluted with 500 ml of water. The mixture was then extracted with 200 ml of ethyl ether, the water layer made alkaline with saturated sodium bicarbonate and extracted 6 times with 400 ml portions of ethyl ether. The ether solution was dried over sodium sulphate and taken to dryness to provide 18 grams of an oil. The oil was dissolved in 80 ml of acetic acid and 80 ml of acetic anhydride and refluxed for 2 hours. The solvent was then removed in vacuo and the residue extracted 4 times with 250 ml portions of ethyl ether. The ether layer was washed with 10% sodium hydroxide and water, dried over sodium sulphate and taken to dryness. The residue was dissolved in 200 ml of methanol and 20 grams of sodium methoxide was used to hydrolyze the acetate groups. After recrystallization from methanol, 6.2 grams of 16-methylene-5$\beta$-androstan-3$\alpha$,7$\alpha$-diol-17-one having a melting point of 174°-178° C. were obtained. The 16-methylene etiocholanolone had an optical rotation of +36°.

EXAMPLE 3

A mixture of 18.6 grams of etiocholanolone, 9.75 grams of paraformaldehyde, 32.5 grams of dimethylamine hydrochloride and 165 ml of isoamyl alcohol was refluxed for 2 hours, cooled to 5° C. and then aged for 16 hours. A mixture of 1:9 hydrochloric acid/water was added with stirring and then diluted with 500 ml of water. Impurities were removed by extraction with 200 ml of ethyl ether and then water layer was made alkaline with saturated sodium carbonate and extracted with ethyl ether. The ether solution was concentrated to dryness and the residual oil was heated with 37 ml of acetic acid and 40 ml of acetic anhydride at 100° C. for 2 hours after which the solvent was removed in vacuo. The residue was extracted with water and ethyl ether and then the ether solution was hydrolyzed with sodium methoxide, taken to dryness and the residue recrystallized from methanol. 5.1 grams of 16-methylene-5$\beta$androstan-3$\alpha$-ol-17-one, having a melting point of 160°-165° C. and an optical rotation of +50.5° C., were obtained.

EXAMPLE 4

The 16-methylene group of the Example 3 product is converted to 16-methyl as follows:

2 grams of the product of Example 2 were dissolved in 20 ml of pyridine, 0.5 gram of palladium on charcoal was added and the mixture was shaken under hydrogen at room temperature for two hours. The resulting mixture was filtered and the solution taken to dryness in vacuo. The solids were then slurried with petroleum ether and recrystallized from methanol. A yield of 0.8 gram of 16-methyl-3$\alpha$, 7$\alpha$-dihydroxy-$\alpha$-ET having a melting point of 120°-125° C. and an optical rotation of +5° was obtained.

EXAMPLE 5

The 16-methylene group of the Example 2 product is converted to 16-methyl as follows:

2 grams of the product of Example 2 were dissolved in 20 ml of pyridine, 0.5 gram of palladium on charcoal was added and the mixture was shaken under hydrogen at room temperature for two hours. The resulting mixture was filtered and the solution taken to dryness in vacuo. The solids were then slurried with petroleum ether and recrystallized from methanol. The product $\alpha$-ET-16-methyl, was obtained in a 0.5 gram yield, had a melting point of 150°-154° C. and an optical rotation of +2°.

EXAMPLE 6

Into 1 ml of pyridine was dissolved 1.8 grams of 16-methylene-$\beta$-ET. 1.16 grams of palmatyl chloride was added and the mixture heated to 100° C. for one hour. Thereafter, the mixture was cooled to room temperature and 20 ml of methylene chloride was added. The product was washed with water, 10% sodium bicarbonate, water and dried over sodium sulphate and then taken to dryness in vacuo. 16-methylene $\beta$-ET palmitate as a waxy solid was obtained in a yield of 2.6 grams.

EXAMPLE 7

A mixture was made of 150 ml of cyclopentanone, 285 ml of orthoformate, 310 of ml of absolute alcohol and 1.425 grams of p-toluenesulfonic acid. The mixture was refluxed for one hour and then cooled to room temperature. After adding 1.05 grams of potassium carbonate and filtering, the liquid was distilled under 20 mm of vacuum and the 68°-71° C. fraction collected. 106 grams of product were obtained.

To 10 ml of the distillate was added 5 grams of 16-methylene $\alpha$-ET. The mixture was heated at 145° C. for three hours and then the temperature was raised to 190° C. for 2 hours. The residue was dissolved in 120 ml of methanol containing a few drops of pyridine. The solution was evaporated in vacuo to 10-15 ml and allowed to crystallize. 3.1 grams of the cyclopentyl ether of 16-methylene-ET having a melting point of 126°-128° C. were obtained.

EXAMPLE 8

The efficacy of the compound of Example 3 has been demonstrated in experiments with mice with diabetes-obesity condition produced by mutant diabetes (db) gene. The severity of the diabetes depends on the background genetic factors inherent in the inbred strains in which the mutations are maintained and expressed. The mice used were C57BL/Ks-db/db mice obtained from the Jackson Laboratory of Bar Harbor, Maine. In these mice, the diabetes mutation elicits an exaggerated obesity and a severe life-shortening diabetes. This diabetes is characterized by hyperplasia and hypertrophy of the beta cells of the islets of Langerhans, followed by severe degranulation and subsequent atrophy of the islets, rising blood glucose concentrations over 400 mg/dl, and death at 5-8 months.

Male mice were used. The mice were divided into groups, one of which was fed chow alone (Old Guilford 96) and others fed the chow into which either DHEA or the Example 3 compound had been incorporated. Incorporation was effected by dissolving the compounds in acetone which was mixed with the food diet, followed by evaporation of the acetone prior to use.

The mice were weighed weekly at the time of bleeding for determination of the blood sugar concentration. Plasma immunoreactive insulin concentrations were quantified periodically during the treatment period and at the time of termination. After sacrifice, the pancreas was removed, weighed and one-half was fixed in Bouin's solution for subsequent histological study and morphometric analysis and the other half homogenized in acid-ethanol (1.5% concentrated HCl in 70% ethanol) to determine the pancreatic insulin content. Blood glucose, immunoreactive insulin (IRI) concentrations and glucose tolerance tests were carried out as described in Coleman, et al, Studies with the Mutation, Diabetes, in the Mouse, Diabetologia 3: 238-248 (1967).

When 16-methylene α-ET was incorporated into the chow at 0.05%, the following results were obtained:

| Time | Blood Glucose | Weight, gm |
| --- | --- | --- |
| Start | 149 ± 3.8 | 22.9 ± 1.2 |
| 4 Weeks | 178 ± 7.2 | 38.5 ± 1.2 |
| 8 Weeks | 178 ± 7.1 | 48.8 ± 1.0 |
| Control (8 Weeks) | 360 ± 8 | 44 ± 1.0 |

When the 16-methylene β-ET was incorporated into the chow at 0.1%, the following results were contained:

| Time | Blood Glucose | Weight, gm |
| --- | --- | --- |
| Start | 149 ± 3.8 | 24.4 ± 1.0 |
| 4 Weeks | 138 ± 6.5 | 34.5 ± 1.4 |
| 8 Weeks | 170 ± 2.0 | 46.7 ± 2.0 |
| Control (8 weeks) | 400 ± 8 | 45 ± 1.0 |

EXAMPLE 9

Erythropoietic Activity

It is known that certain steroids are porphyrogenic, i.e. they induce porphyrin synthesis and induce heme formation in cells. The test system used in investigations of this activity is the primary avian liver cell culture system described by Granick and Kappas, J. Boil, Chem. 242, 4587-93 (1967). In accordance with this technique, livers of 16 to 17 day old chick embryos are minced, and the cells separated by trypsin. Suspension containing 3 to $5 \times 10^5$ cells are inoculated into vials which contain a cover slip and 1.0 ml. of Eagle's basal medium supplemented with glutamine, fetal bovine serum, and antibiotics. The vials are incubated at 37° C. in 5% CO$_2$ and air for 24 hours. The medium is then replaced, and the addition of the steroid is made as required. Following reincubation for an additional 20 to 22 hours, the cover slips, now overgrown with a monolayer of hepatic parenchymal cells, are examined under phase and fluorescence optics. Semi-quantitative estimates of cellular porphyrins are made on the basis that values of fluorescence intensity ranging from +1.0 to +4.0 are equivalent to approximately 5 to $50 \times 10^{-11}$ moles of protoporphyrin per mg. of protein on the cover slip.

The compound of Example 3 and α-ET are tested for induction of porphyrin synthesis using the foregoing technique in cultured chick embryo cells. The 16-methylene compound of Example 3 is more effective than α-ET.

EXAMPLE 10

A typical tablet containing a compound of the invention contains 200 mg 16-methylene βET, 160 mg microcrystalline cellulose, 8 mg of stearic acid and 2 mg of colloidal silica.

EXAMPLE 11

A typical parenteral formulation containing a compound of the invention contains 10 mg of 16-methylene βET and 30 mg of glycine as sterile solids in an ampoule. The ampoule is mixed with 3 ml of diluent (propylene glycol) just before use.

Various changes and modifications can be made in the compounds and processes of the present invention without departing from the spirit and scope thereof. The various embodiments which have been described herein have been for the purpose of further illustrating the invention but were not intended to limit it.

What is claimed is:

1. A compound selected from the group consisting of 16-methylene-5β-androstan-3α-ol-17-one, and 16-methylene-5β-androstan-3α,7α-diol-17-one, and 16-methyl-5β-androstan-3α,7α-diol-17-one.

2. 16-methylene-5β-androstan-3α-ol-17-one in accordance with claim 1.

3. 16-methylene-5β-androstan-3α,7α-diol-17-one in accordance with claim 1.

4. 16-methyl-5β-androstan-3α,7α-diol-17-one in accordance with claim 1.

5. A method of inducing an anti-diabetic, anti-obesity or erythropoietic effect in a mammal which comprises administering to the mammal an anti-diabetic, anti-obesity or erythropoietic effective amount of a compound of claim 1.

6. The method of claim 5, wherein said administration is oral.

7. The method of claim 5, wherein the amount administered is about 100-4,000 mg per 70 kilos.

8. The method of claim 7, wherein the amount is about 500-1,000 mg.

9. The method of claim 5, wherein the administration is parenteral.

10. The method of claim 9, wherein the amount of administration is about 700-2,000 mg per 70 kilos per day.

11. The method of claim 10, wherein the amount is 900-1,100 mg.

12. The method of claim 5, wherein said compound is and 16-methylene-5β-androstan-3α-ol-17-one.

13. The method of claim 5, wherein said compound is 16-methylene-5β-androstan-3α,7α-diol-17-one.

14. A composition comprising an anti-diabetic, anti-obesity or erythropoietic effective amount of a compound of claim 1 in combination with a pharmaceutically acceptable carrier.

15. The composition of claim 14, wherein each unit dose contains about 100-1,000 mg of said compound.

16. The composition of claim 15, wherein each unit dose contains about 200-400 mg.

17. The composition of claim 14, wherein said compound is 16-methylene-5β-androstan-3α-ol-17-one.

18. The compound of claim 14, wherein said compound is 16-methylene-5β-androstan-3α,7α-diol-17-one.

* * * * *